United States Patent [19]

Loza et al.

[11] Patent Number: 4,836,283

[45] Date of Patent: Jun. 6, 1989

[54] DIVALENT ION TOLERANT AROMATIC SULFONATES

[75] Inventors: Roman Loza, Solon; Arthur J. Cooper, Garfield Heights; Gerald P. Coffey, Lynnhurst, all of Ohio

[73] Assignee: The Standard Oil Company, Cleveland, Ohio

[21] Appl. No.: 204,061

[22] Filed: Jun. 8, 1988

[51] Int. Cl.$^4$ .............................................. E21B 43/22
[52] U.S. Cl. ................................. 166/225; 252/8.554
[58] Field of Search ................ 166/273, 274, 275; 252/8.554

[56] References Cited

U.S. PATENT DOCUMENTS

| | | |
|---|---|---|
| 3,500,923 | 3/1970 | Reisberg . |
| 3,675,716 | 7/1972 | Farmer, III et al. . |
| 3,811,504 | 5/1974 | Flournoy et al. . |
| 3,811,505 | 5/1974 | Flournoy et al. . |
| 3,811,507 | 5/1974 | Flournoy et al. . |
| 3,916,994 | 11/1975 | Maddox, Jr. et al. . |
| 3,939,911 | 2/1976 | Maddox, Jr. et al. . |
| 3,977,471 | 8/1976 | Gale et al. . |
| 4,013,569 | 3/1977 | Chiu et al. ..................... 252/8.554 |
| 4,018,278 | 4/1977 | Shupe . |
| 4,076,743 | 2/1978 | Koch et al. . |
| 4,090,969 | 5/1978 | Koch et al. . |
| 4,130,491 | 12/1978 | Wagner et al. . |
| 4,171,323 | 10/1979 | Marin et al. ............... 252/8.554 X |
| 4,181,178 | 1/1980 | Savins . |
| 4,193,452 | 3/1980 | Wilson et al. . |
| 4,216,097 | 8/1980 | Stournas . |
| 4,231,427 | 11/1980 | Kalfoglou . |
| 4,259,191 | 3/1981 | Wagner . |
| 4,269,271 | 5/1981 | Shupe et al. . |
| 4,270,607 | 1/1981 | Cardenas et al. . |
| 4,293,428 | 10/1981 | Gale et al. . |
| 4,296,812 | 10/1981 | Kalfoglou . |
| 4,307,782 | 12/1981 | Schievelbein . |
| 4,326,809 | 2/1982 | Griffith et al. . |
| 4,436,672 | 3/1984 | Naylor ............................ 166/274 X |
| 4,452,708 | 6/1984 | Aldrich et al. ................... 252/8.554 |
| 4,454,074 | 6/1984 | Naylor ........................... 252/8.554 X |
| 4,468,335 | 8/1984 | Chen et al. . |
| 4,468,342 | 8/1984 | Chen . |
| 4,469,604 | 9/1984 | Stapp et al. . |
| 4,478,281 | 10/1984 | Balzer et al. . |
| 4,485,873 | 12/1984 | Balzer et al. . |
| 4,497,717 | 2/1985 | Bretherick et al. .............. 252/8.554 |
| 4,507,211 | 3/1985 | Naylor et al. ................... 252/8.554 |
| 4,524,023 | 6/1985 | McCoy et al. ............... 252/8.554 X |
| 4,554,974 | 11/1985 | Kalpakci et al. . |
| 4,609,478 | 9/1986 | Egan . |
| 4,643,253 | 2/1987 | Shepherd, Jr. et al. . |
| 4,648,984 | 3/1987 | Krause et al. . |
| 4,699,214 | 10/1987 | Angstadt ..................... 252/8.554 X |

FOREIGN PATENT DOCUMENTS

| | | |
|---|---|---|
| 1086046 | 9/1980 | Canada ............................ 252/8.554 |
| 3520709 | 6/1985 | Fed. Rep. of Germany . |
| 3530405 | 8/1985 | Fed. Rep. of Germany . |
| 3422613 | 12/1985 | Fed. Rep. of Germany ... 252/8.554 |

OTHER PUBLICATIONS

Determination of Anionic-Active Detergents by Two-Phase Tritration V. Reid et al., CIA report 1967.
Aqueous Surfactant Systems for Oil Recovery H. Hill et al., J. Pet. Tech. 1973.
A Low-Tension Waterflooding Process, W. Foster, 1973.

Primary Examiner—George A. Suchfield
Attorney, Agent, or Firm—Michael F. Esposito; David J. Untener; Larry W. Evans

[57] ABSTRACT

Divalent ion tolerant aromatic sulfonate suitable for enhanced oil recovery characterized by the formula:

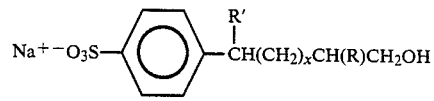

wherein
x=0 to 4
R'=H or CH$_3$
R=CH$_3$(CH$_2$)y and y=1 to 15. Preferably, the composition comprises of second compound characterized by the formula

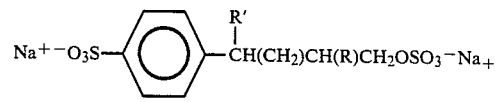

wherein R, x, y, and R' are the same as defined in claim 1.

2 Claims, No Drawings

4,836,283

DIVALENT ION TOLERANT AROMATIC SULFONATES

BACKGROUND OF THE INVENTION

The present invention is related to a novel surfactant of use in enhanced oil recovery. In particular, the present invention is directed to alky/aryl alcohols having been sulfonated on the aromatic ring with the alcohol having an alkyl branched side chain.

The present surfactants are also useful in many industrial applications, such as acid and alkaline cleaners and degreasers, acid pickling baths, textile scouring agents, fiber processing aids, scale inhibition, and metal plating.

In the recovery of oil from oil bearing reservoirs, it is usually possible to recover only minor portions of the original oil by so called primary recovery methods which utilize only the natural forces present in the reservoir. A variety of supplementary recovery techniques have been employed in order to increase the recovery of oil from subterranean reservoirs. The most widely used supplemental recovery technique is water flooding which involves injection of water into the reservoir. As the water passes through the reservoir, it acts to displace the oil trapped in the reservoir system leading to an enhanced recovery of oil.

It has long been recognized that factors such as interfacial tension between the injected water and the reservoir oil, the relative mobilities of the reservoir oil and injected water, and the wettability characteristics of the rock surfaces within the reservoir are factors which influence the amount of oil recovered by water flooding. It has been proposed to add surfactants to the flood water in order to lower the oil-water interfacial tension and/or to alter the wettability characteristics of the reservoir rock. Processes which involve the injection of aqueous surfactant solutions are commonly referred to as surfactant water-flooding or as low tension water-flooding. Also, it has been proposed to add viscosities such as polymeric thickening agents to all or part of the injected water in order to increase the viscosity thereof, thus decreasing the mobility ratio between the injected water and oil and improving the sweep efficiency of the water-flood.

A problem with stability and effectiveness arises with these products when they are used in environments characterized by temperatures in the range of 70° C. to 120° C. and above, high pressures (e.g. 4,000 psi), and high concentrations of divalent metals such as calcium, magnesium, etc. (e.g. up to 3,000 ppm or more) and high salt content.

Many water-flooding applications have employed anionic surfactants. For example, a paper by W. R. Foster entitled "A Low-Tension water-flooding Process", *Journal of Petroleum Technology*, Vol. 25, February 1973, pages 205-210, describe the technique involved in the injection of an aqueous solution of petroleum sulfonates within designated equivalent weight ranges and under controlled conditions. The petroleum sulfonate plug is followed by a thickened water plug which contains a viscosifier such as a water soluble biopolymer. This thickened plug is then following by a driving fluid such as a field brine which is injected as necessary to carry the process to conclusion.

One problem encounted in water-flooding with certain anionic surfactants such as the petroleum sulfonate is the lack of stability of the surfactants in so-called "hard water" environments. These surfactants tend to precipitate from solution in the presence of relatively low concentrations of divalent metal ions such as calcium and magnesium. For example, divalent metal ion concentrations of about 50-100 ppm and above usually tend to cause precipitation of petroleum sulfonates.

Nonionic surfactants such as polyethoxylated alkyl phenols, polyethoxylated aliphatic alcohols, carboxylic esters, carboxylic amides, and polyoxyethylene fatty acid amides, have a somewhat higher tolerance to polyvalent ions such as calcium or magnesium than do the more commonly utilized anionic surfactants. While it is technically feasible to employ the nonionic surfactant solution to decrease the interfacial tension between the border displacement medium and petroleum contained in the reservoir such use is generally not economically feasible for several reasons. First, nonionic surfactants are not as effective on a per mole basis as are the more commonly anionic surfactants and, additionally, the nonionic surfactants generally have a higher cost per unit weight than do the anionic surfactants.

The use of certain combination of anionic and nonionic surfactants to combat hard water formations has also been suggested. For example, U.S. Pat. No. 3,811,505 discloses the use of alkyl or alkylaryl sulfonates or phosphates and polyethoxylated alkyl phenols. U.S. Pat. No. 3,811,504 and 3,811,507 disclose other surfactants used for this type of oil recovery.

The use of certain amphoteric surfactants which function as cationics in acid medium and become anionic when incorporated in alkaline systems has also been suggested. For example, U.S. Pat. No. 3,939,911 discloses a surfactant water-flooding system employing a three component surfactant system. This surfactant system includes an alkyl or alkylaryl sulfonate such as an ammonium dodecyl benzene sulfonate, a phosphate ester sulfonate and a sulfonated betaine. Finally, the use of hydrocarbyl-substituted polyoxyalkylene sulfonates has been disclosed in U.S. Pat. Nos. 3,916,994; 4,181,178; 4,231,427; 4,269,271; 4,270,607; 4,296,812; 4,307,782; 4,316,809; 4,485,873; and 4,478,281.

Recently, U.S. Pat. Nos. 4,468,335 and 4,468,342 have issued which disclose the use of branched alkyl-substituted polyethoxy propane sulfonates used for enhanced oil recovery. In addition, U.S. Pat. No. 4,469,605 to Stapp et. al has disclosed the use of sulfonated phenolic compounds as well as sulfomethylated compounds as surfactant systems in post oil recovery procedures.

While many surfactant water-flooding methods have been disclosed there is a substantial unfilled need for surfactants and water-flooding methods employing such surfactants that are useful in recovering oil from subterranean formations wherein the surfactant employed are suitable in harsh environments, in particular, environments where there is a high concentration of divalent ions such as magnesium and calcium. The present invention offers surfactants suitable in this type of environment.

SUMMARY OF THE INVENTION

It is the primary object of the present invention to provide a novel surfactant for use in enhanced oil recovery.

It is another object of the present invention to provide a process for enhanced oil recovery of oil entrapped in subterranean reservoirs utilizing the surfactant of the present invention.

Additional objects, advantages and novel features of the invention will be set forth in the description that follows, and in part will become apparent of those skilled in the art upon examination of the following or may be learned by practice of the invention. The objects and the advantages of the invention may be realized and obtained by meanings of the instrumentalities and combinations particularly pointed out in the pending claims.

To achieve the foregoing objects and in accordance of the purpose of the present invention as embodied and described herein, the surfactant is characterized by the following formula:

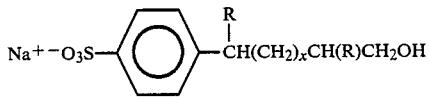

where
x=0 to 4
R'=H or CH$_3$
R=CH$_3$(CH$_2$)y and y=1 to 15, preferably 3 to 11, especially preferred is y=4 to 10

In a preferred embodiment of the present invention the surfactant is characterized by the formula recited above where x equals 0 to 1, most preferably x equals 0 and R' equals H.

In a further embodiment of the present invention the surfactant comprises a mixture of a compound having the formula as set forth above and a second surfactant having the following formula:

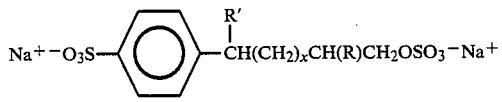

where R, R' x and y are defined in formula 1, above.

In a further aspect of the present invention a method for recovering oil from subterranean formation comprises injecting into the formation an aqueous composition comprising a surface active amount of the composition a compound represented by Formula 1 set forth above to drive the oil present in the subterranean formation out of the formation to a production well where said oil can be recovered.

In a preferred aspect of this embodiment of the present invention the surfactant utilized to recover the oil in the subterranean formation is a mixture of Formula 1 and Formula 2 as set forth above.

The enhanced oil recovery surfactant of the present invention is specific to overcoming the problems associated with the use of surfactants which are sensitive to divalent metal ions. The surfactants of the present invention are unexpectfully tolerant to the presence of divalent ions. The novel surfactants of the present invention required that sulfonation must be on the aromatic ring and that the alcohol component has to have an alkyl branched side group as defined above. It has been discovered that the surfactants of the present invention are able to tolerate divalent ion presence in the order of greater than 20,000 ppm. By contrast conventional commercial sulfonates such as dodecylbenzene sulfonate (SDBS) can only tolerate 100 ppm divalent ion. In addition, the sulfonated alkyl phenols disclosed in U.S. Pat. No. 4,469,604 have been found to be stable to only 160 ppm divalent ion concentration. The surfactants of the present invention represent over a 100,000 percent improvement in stabilization to the presence of divalent ions which should lead to enhanced oil recovery in the presence of the divalent ions.

DETAILED DESCRIPTION OF THE INVENTION

The surfactants of the present invention may be prepared by sulfonating 2-benzylalkanols or 2-alkyl,5-phenylhexanol. The alcohols may be prepared by aldol condensation/reduction or Guerbet condensation, both known reactions. The preferred surfactants of the present invention are prepared in two steps. In the first step benzyl alcohol (3) is condensed (Guerbet reaction) with a linear alcohol (e.g. octanol, (4) according to following equation.

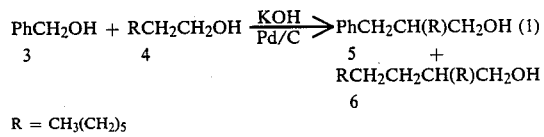

R = CH$_3$(CH$_2$)$_5$

The catalyst for the condensation is palladium on carbon and 20% mole% potassium hydroxide. Potassium benzoate and water are the main by-products. A large excess of benzyl alcohol (1) is used to maximize the yield of (5). For a more detailed description of the conditions and reactants suitable for the preparation of the alcohols by the Guerbet reaction reference is made to U.S. Pat. No. 4,648,984 herein incorporated by reference.

A mixture of two products is obtained: 2-benzyloctanol (5) and 2-hexyldecanol (6). This mixture is then sulfonated using a solution of chlorosulfonic acid in methylene chloride. After sulfonation the reaction mixture is hydrolyzed and unreacted materials and manufactured by-products are removed along with the methylene chloride. What is left is an aqueous solution (pH=6-7) of surfactant (15% active). Analysis of the product shows that it is composed of a mixture of two aromatic sulfonates. The major component (50-100%) is an alcohol sulfonate (7) having the following structure:

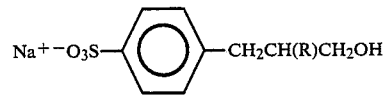

R = CH$_3$(CH$_2$)$_5$

In addition, a smaller, and variable (0–50%), amount of a second surfactant is present. This compound (shown below) is a sulfate sulfonate (8).

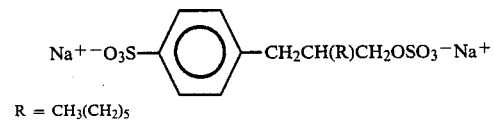

R = CH$_3$(CH$_2$)$_5$

Five alkyl/aryl alcohols utilized to produce the surfactants of the present invention and two alkylphenols (for comparison purposes) were sulfonated using chlorosulfonic acid (HSO$_3$Cl). In each of these examples the chlorosulfonic acid was added slowly (1–2 h) at 0°–4° C. to a methylene chloride solution of the alcohol (phenol) followed by warming to 22° C. and stirring for an additional 3 h. Table 1 below summarizes the experimental conditions used in the various sulfonation reactions.

The reaction was quenched by pouring the sulfonation mixture into ice-water. The pH was adjusted (6 to 8) with sodium bicarbonate and isopropanol was added. Petroleum (pet) ether extraction was used to remove unsulfonated alcohol and other nonionic by-products. Removal of the volatiles from the aqueous phase gave the desired sulfonate surfactant along with a considerable amount of inorganic salts. The crude sulfonation mixture was desalted by saturating (at 60° C.) a water-/isopropanol solution of the surfactants with sodium chloride. The surfactant is extracted into the isopropanol—which separates from the brine. Removal of the solvent gave the surfactant.

The crude product from the sulfonation reaction of alcohols contained two components. The major component was the disodium salt of the ring sulfonated alkyl-/aryl alcohol sulfate (referred to as the sulfate/sulfonate). The minor one was the sodium sulfate of alcohol (8). Acid hydrolysis (0.14M HCl at 82° C. for 24 h) converted the majority of sulfate/sulfonate to alcohol/-sulfonate. The major product in the sulfonation reaction of alcohols was sulfate/sulfonate.

Rather than isolating then hydrolyzing sulfate/sulfonate a more convenient procedure was to quench the sulfonation reaction with water and use the acids generated (HCl and $H_2SO_4$) to hydrolyze the sulfate/sulfonate. Using this procedure, the 2-alkyl-5-phenylhexanols gave 65–84% alcohol/sulfonate. In comparison, the 2-benzylalkanols gave only 20 to 50% alcohol/sulfonate.

TABLE 1

Sulfonation of Alkyl/Aryl Alcohols: Reaction Conditions, Product Purity, and Product Key Used in the Text.

| Examples | Main Component (Alcohol) for Starting Sulfonation | Reaction Temperature °C. | Hydrolyzed? | Desalted |
|---|---|---|---|---|
| Example 1 - 71-2[a] | 2Hexyl-5-phenylhexanol I | 0–23 | Y | Y |
| Example 2 - 63-2 | 2-Pentyl-5-phenylhexanol J | 0–23 | Y | Y |
| Example 3 - 92-2[b] | 2-Octyl-5-phenylhexanol L | 0–23 | Y | Y |
| Example 4 - 89-2 | 2-Benzyloctanol M | 0–23 | Y | Y |
| Example 5 - 96-1 | 2-Benzyldecanol Q | | Y | Y |
| Comparative Example 1 - 32-3 | 4-Dodecylphenol R | 0 | N | Y |
| Comparative Example 2 - 67-2 | 4-Nonylphenol T | 0–23 | Y | Y |

[a] 71-2 was hydrolyzed until no change in surfactant concentration was observed by two-phase titration.
[b] 92-2 starting alcohols were distilled before sulfonation.

As mentioned above, surfactants for EOR must be compatible with divalent ion containing brines such as seawater. Solubility tests were carried out in both deionized water and in seawater. The results of these experiments are summarized in Table 2 below. The surfactants of this invention (Examples 1–5) were all soluble in seawater. The sulfonated alkylphenols of prior patent (U.S. Pat. No. 4,469,605) (Comparative Examples 1 and 2) were either insoluble or partially soluble in seawater. A commercial sulfonate (SDBS, Comparative Example 3) was insoluble in seawater. All surfactants were soluble in distilled water.

Calcium-ion tolerance tests were conducted to quantify the relative solubility of the surfactants in the presence of divalent ions (see Table 2). All of the surfactants of this invention tolerated calcium ion concentrations from 28 to 10,000 times higher than the comparative examples.

TABLE 2

Surfactant Properties of Alkyl/Aryl Sulfonates.

| Surfactant | 60° C. Solubility (@ mEq/L)[d] | | Calcium Precipitation (ppm $CA^{2+}$)[e] | Surface Tension (Dyne/cm)[f] |
|---|---|---|---|---|
| | $H_2O$ | Seawater | | |
| Example 1: I | S(18) | A(27) | 2800 | 25.1 |
| Example 2: J | S(35) | S(34) | 355,20K[g] | 25.6 |
| Example 3: L | S(18) | S(27) | 40K | 26.4 |
| Example 4: M | S(15) | S(26) | 350,57K[g] | 25.2 |
| Example 5: Q | S(15) | S(27) | 100K | 29.3 |
| Comparative Example 1: R | S(24) | I(25) | <80 | 23.4 |
| Comparative Example 2: T | S,T(30) | P(28) | 160 | 24.9 |
| Comparative Example 3: | S(27) | I(27) | 90 | 28.6 |

TABLE 2-continued

Surfactant Properties of Alkyl/Aryl Sulfonates.

| Surfactant | 60° C. Solubility (@ mEq/L)$^d$ H$_2$O | Seawater | Calcium Precipitation (ppm CA$^{2+}$)$^e$ | Surface Tension (Dyne/cm)$^f$ |
|---|---|---|---|---|
| SDBS | | | | |

$^d$S = completely soluble P = partially soluble I = insoluble T = turbid solution
$^e$A 10 mEq/L solution of Surfactant was titrated with 5 M CaCl$_2$ solution until the transmittance of the solution (600 nm) was reduced to 80% of the initial value.
$^f$Of a 10 mEq/L solution of surfactant at 22° C.
$^g$One component apparently precipitates out at the lower calcium ion concentration and the remainder at the higher calcium concentration.

The surface activity—lowering of the air/water surface tension—of the surfactants was also measured. Surface tensions were measured at a surfactant concentration of 10 milliequivalents/L in deionized water at 22° C. or a Fisher Autotensiomat (de Nouy ring) apparatus. At this concentration, all the surfactants should be above their critical micell centration (CMD) and should give maximum surface tension lowering. The values measured are all in the range of 23–30 dynes/cm. typical for anionic surfactants (see Table 3).

As further illustration of the practice of the present invention the following examples were prepared.

EXAMPLES 6 AND 7

The reaction products of the Guerbet reaction of benzyl alcohol and octanol (i.e. a mixture of 2-benzyloctanol (5) and 2-hexyldecanol (6)) was sulfonated using a solution of chlorosulfonic acid in methylene chloride. After sulfonation the reaction mixture is hydrolyzed and unreacted materials and nonsurfactant by-products are removed along with the methylene chloride. What is left is an aqueous solution (pH=6-7) of surfactant (15% active). Analysis of the product shows that it is composed of a mixture of two aromatic sulfonates. The major component (50–100%) is an alcohol sulfonate having the following structure:

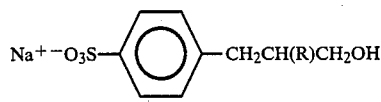

R = CH$_3$(CH$_2$)$_5$

In addition, a smaller and variable (0–50%), amount of a second surfactant is present. This compound (shown below) is a sulfate sulfonate having the formula:

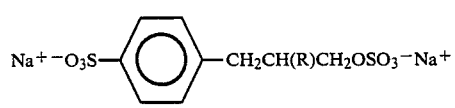

R = CH$_3$(CH$_2$)$_5$

The product obtained from this example was designated DIVIT 800. The procedure was repeated using a mixture derived from the Guerbet Reaction of benzylalcohol and decanol. This product was designated DIVIT 1000.

Below is a short summary of the physical properties and selected performance data of the DIVIT surfactants.

Physical Form:
DIVIT-800/100 surfactants are available as aqueous solutions (15% active).

Molecular Weight:
DIVIT-800: 322
DIVIT-1000: 350
SDBS: 348 Data on SDBS (sodium dodecylbenzenesulfonate), a commercial surfactant (Siponate ® DS-10), is presented for reference.

Surface tensions (in dynes/cm) were measured using the Du Nouy ring method. The reported surface tensions are for 10 meq/L surfactant solutions: which is above the CMC (critical micelle concentration). The CMC's (in meq/L) were determined by examination of surface tension vs. surfactant concentration curves. The results are set forth below in Table 3.

TABLE 3

| Surfactant | Calcium Ion Concentration | CMC | Surface Tension |
|---|---|---|---|
| DIVIT-800 | 0 | 10 | 25 |
| | 1000 PPM | 0.2 | 24 |
| | 10,000 PPM | 0.2 | 24 |
| DIVIT-1000 | 0 | 1 | 29 |
| | 1000 PPM | 0.2 | 25 |
| | 10,000 | 0.2 | 25 |
| SDBS | 0 | 1 | 29 |
| | 1000 PPM | NA | surfactant precipitate |
| | 10,000 PPM | NA | surfactant precipitate |

Foam Formation/Stability

Foam tests were conducted using a simple version of the Ross-Miles foam test. The initial (0 min) foam volume for SDBS was assigned a value 100. All other foam volumes were related to this value. This results are summarized below in Table V. Surfactant concentration was 10 meq/L.

| Time | Surfactant SDBS | DIVIT-800 | Foam Volume DIVIT-1000 |
|---|---|---|---|
| 0 min | 100 | 60 | 54 |
| +5 min | 94 | 49 | 49 |
| +15 min | 83 | 43 | 49 |
| +30 min | 77 | 31 | 46 |
| +45 min | 71 | 26 | 40 |

Thermal Stability:

Surfactant solutions were prepared in distilled water, 1.2M sodium hydroxide, and 1.2M hydrochloric acid. These solutions were aged at 90° C. Samples were withdrawn at regular interval and surfactant activity was determined by two-phase titration. The results were summarized below in Table IV.

TABLE IV

| Solution | Time (hr) | Surfactant Activity (%) SDBS | DIVIT-800 | DIVIT-1000 |
|---|---|---|---|---|
| Distilled Water | 0 | 100 | 100 | 100 |
| | 330 | 93 | 100 | 98 |
| | 525 | 93 | 100 | 98 |

TABLE IV-continued

| Solution | Time (hr) | SDBS | Surfactant Activity (%) DIVIT-800 | DIVIT-1000 |
|---|---|---|---|---|
| | 740 | 93 | 105 | 94 |
| | appearance | clear | cloudy | clear |
| 1.2 M NaOH | 0 | 1 | 100 | 100 |
| | 305 | — | 100 | 100 |
| | 500 | — | 94 | 100 |
| | 720 | — | 94 | 97 |
| | appearance | ppt | ppt | ppt |
| 1.2 M HCl | 0 | 100 | 100 | 100 |
| | 305 | 92 | 94/100 | 98 |
| | 500 | 59 | 100 | 98 |
| | 720 | 41 | 100 | 94 |
| | appearance | ppt | clear | clear |

The foregoing description of the preferred embodiment of the present invention has been presented for illustration and description. It is not intended to be exhaustive of the invention described. Even though, these surfactants are intended as EOR surfactants the high solubility of these materials in divalent-ion brines makes them an attractive specialty surfactant for other purposes such as metal cleaner, acid cleaning solutions, emulsion polymerization, metal plating additives and scale inhibition.

What is claimed is:

1. The process of recovery of hydrocarbons present in a subterranean formation comprising injecting a surfactant composition containing a compound having the formula:

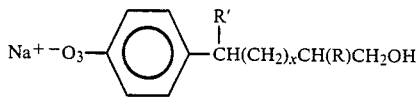

where
x=0 to 4
R'=H or CH$_3$
R=CH$_3$(CH$_2$)y and y=1-15 into an injection well whereby said composition causes said hydrocarbon present in said injection well to be displaced into one or more production wells, and
(b) recovering said displaced hydrocarbon from at least one of said production wells.

2. The process of claim 1 wherein said composition further comprising a compound having the formula:

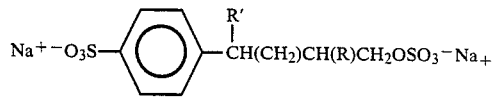

wherein R, x, y, and R' are the same as defined in claim 1.

* * * * *